United States Patent [19]

Dias

[11] Patent Number: 5,060,653

[45] Date of Patent: Oct. 29, 1991

[54] ULTRASONIC SENSOR WITH STARVED DILATATIONAL MODES

[75] Inventor: J. Fleming Dias, Palo Alto, Calif.

[73] Assignee: Hewlett-Packard Company, Palo Alto, Calif.

[21] Appl. No.: 352,807

[22] Filed: May 16, 1989

[51] Int. Cl.[5] .............................................. A61B 8/00

[52] U.S. Cl. ................................ 128/662.03; 310/336

[58] Field of Search ...................... 128/660.01, 661.01, 128/662.03; 310/334, 336; 73/625, 626; 29/25.35

[56] References Cited

U.S. PATENT DOCUMENTS

| | | | |
|---|---|---|---|
| 4,101,795 | 7/1978 | Fukumoto et al. | 128/662.03 X |
| 4,240,003 | 12/1980 | Larson, III | 128/662.03 X |
| 4,385,255 | 5/1983 | Yamaguchi et al. | 128/662.03 X |
| 4,442,715 | 4/1984 | Brisken et al. | 128/661.01 X |

OTHER PUBLICATIONS

"An Annular Array System for High Resolution Brease Echography", by M. Arditi, W. B. Taylor, F. S. Foster and J. W. Hunt; *Ultrasonic Imaging 4,* 1982, pp. 1–31.

*Primary Examiner*—Francis Jaworski

[57] ABSTRACT

A method and apparatus to improve the performance of an ultrasonic imaging sensor [11] is disclosed. The key to the performance improvement obtained in the present invention is in the matching of sensor element [10] size to the electrical characteristics of the train of pulses [24,32] used to drive the sensor. The matching causes essentially all the energy provided to the sensor [11] to go into the desired sensor resonances, those in the direction of the sensor's thickness dimension [12]. The matching also minimizes the energy which goes into the undesired dilatational resonance modes [16,18] those in the sensor element's width dimension [14]. The invention discloses the matching of each sensor element [10] so that its maximum dilatational response [54] is essentially at the same frequency as every other element in the array, so that dilatational response is substantially reduced for the array as a whole. The invention also disclosed the "fine tuning" of the frequency of the drive pulses, so that the dilatational response is further reduced. The invention therefore permits the fabrication of ultrasonic sensor arrays [11], having high sensitivity, freedom from spurious returns, and low noise signals.

14 Claims, 6 Drawing Sheets

ULTRASONIC SENSOR WITH STARVED DILATATIONAL MODES

BACKGROUND OF INVENTION

The present invention is a method and apparatus to improve the performance and efficiency of ultrasonic sensors which are used for such important tasks as non-invasive medical imaging and non-destructive industrial testing, such as checking the safety of nuclear power plants.

Ultrasonic imaging sensors act as both transmitters and receivers of ultrasonic energy. The sensor first acts as a transmitter; emitting ultrasonic energy in a train of high frequency pulses, typically in the range of 2 to 10 Mhz. Then the transmitter is turned off and the sensor acts as a receiver, which listens for returned echoes at the transmitted frequency.

A high performance ultrasonic sensor must be sensitive, accurate and have a low level of spurious acoustic responses including noise when excited by a short drive pulse. An acoustic pulse obtained from a short drive pulse gives good axial resolution, but it has a very broad frequency spectrum. The broad frequency spectrum excites spurious acoustic resonances called modes within the sensor. These modes tend to degrade its frequency response and consequently its ability to accurately differentiate closely spaced targets or impedance discontinuities when imaging parts of the human body. A system consisting of an imaging sensor and the associated electronic circuitry must be capable of transmitting the broadest range of frequencies by eliminating or suppressing the spurious modes, so as to enhance its sensitivity to detect the desired targets.

Existing ultrasonic sensors are designed to have a particular resonant frequency, which is the frequency at which desired mechanical motion is maximized. At that resonant frequency, the sensor elements are intended to vibrate along a preferred direction of sound propagation. However, driving the sensor at the desired resonant frequency will cause some of the energy to be coupled orthogonally to the desired motion. Such orthogonal motions represent sources of spurious modes in an imaging transducer. For example, if the sensor is in the form of a flat plate, the desired motion, or resonance, is in its thickness dimension. Undesired motions, called dilatational resonance modes, or dilatational modes, occur along the length and width of the plate.

The frequency of the modes is inversely proportional to these dimensions. Consequently, if the width is close to the thickness dimension, the spurious dilatational mode will fall close to the pass band of the thickness mode. This is shown in FIG. 2 for the element shown in FIG. 1.

Depending on whether the width is greater than, or less than, the thickness, the spurious modes will fall below or above the main resonance. The length dimension is usually much greater than the width, so that the spurious length mode is of very low frequency.

Both situations exist in medical sensors. In an annular array sensor, whose aspect ratio is less than unity, the spurious modes are below the desired response, as shown in FIGS. 2 through 5. In linear arrays, where the aspect ratio is greater than unity, the spurious modes are above the desired response.

In either case, these modes will lengthen the acoustic pulse transmitted into the body, and degrade the axial resolution. Accurate axial resolution translates into an ability to see fine details of tissue structure, and provides the physician a powerful diagnostic tool.

A dilatational mode along the width is shown in FIG. 1. These undesired motions cause energy to be radiated into, and received from, directions other than that intended. The result is that returns are received from undesired directions, and these unwanted returns constitute noise. This unwanted noise is mixed in with the desired signals, thereby degrading the received signals.

The development of an effective method of suppressing the undesirable dilatational modes would constitute a major technological advance in the technology of ultrasonic imaging. The improved performance that would result from such an innovation would substantially improve the performance of ultrasonic imaging equipment used for medical imaging and for important industrial applications.

SUMMARY OF THE INVENTION

The Ultrasonic Sensor with Starved Dilatational Modes disclosed and claimed in this patent application overcomes the problem of undesired dilatational modes. The keys to the success of this invention are:

(a) designing each of the sensor elements in the array to have a particular specified ratio between their thickness and their width, the sensor's "aspect ratio", and (b) using a pulse train having a precise number of pulses to drive the ultrasonic sensor. The number of pulses in the pulse train is chosen to match the sensor's aspect ratio. When the optimum number of pulses is used in the pulse train, very little energy is available at the dilatational modes' frequencies, and the dilatational modes of the sensor are significantly reduced. The energy can be further "fine tuned" by adjusting small variations the frequency of the pulses.

The Applicant's Ultrasonic Sensor with Starved Dilatational Modes provides much better imaging performance than existing ultrasonic sensors. This innovative method and apparatus provides a powerful tool that will enable medical personnel, industrial technicians, and other users of ultrasonic sensors to obtain detailed, noise-free ultrasonic imagery with ease and convenience.

An appreciation of other aims and objectives of the present invention and a more complete and comprehensive understanding of this invention may be achieved by studying the following description of a preferred embodiment and by referring to the accompanying drawings.

BRIEF DESCRIPTION OF THE DRAWINGS

FIG. 2 refers to a sensor element having an aspect ratio (thickness dimension divided by width dimension) of 0.90. FIGS. 3, 4, and 5 have aspect ratios of 0.80, 0.60, and 0.40, respectively.

DESCRIPTION OF THE PREFERRED EMBODIMENT

Figure 1A:
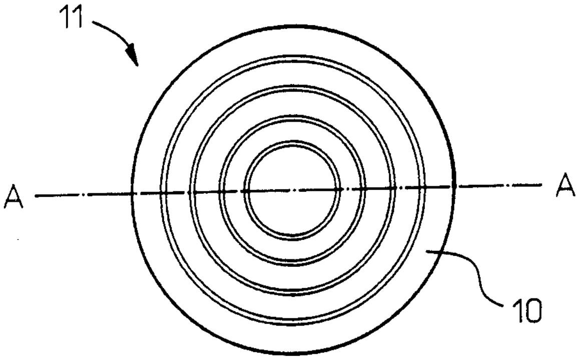
FIG. 1A is a plan view of an annular array sensor of the spherical-shell type which is made in accordance with the teachings of the present invention.
Figure 1B:
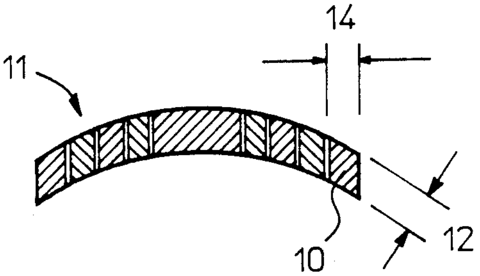
FIG. 1B is a sectional view of a portion of the sensor between section lines A—A of FIG. 1A.

With reference to FIGS. 1A and 1B, the cross section through an individual element [10] of an ultrasonic annular array [11] is generally rectangular in shape, having a thickness dimension [12] which is less than its width dimension [14]. It is desired that ultrasonic waves generated in the transducer radiate in the direction of the thickness dimension [12], i.e. normal to the width dimension, [14], and that no energy be radiated in the direction of the width dimension [14].

Energy radiated in the direction of the width dimension [14] is due to dilatational modes. The present invention reduces the energy radiated in the width dimension [14] by a combination of design techniques.

Figure 2:
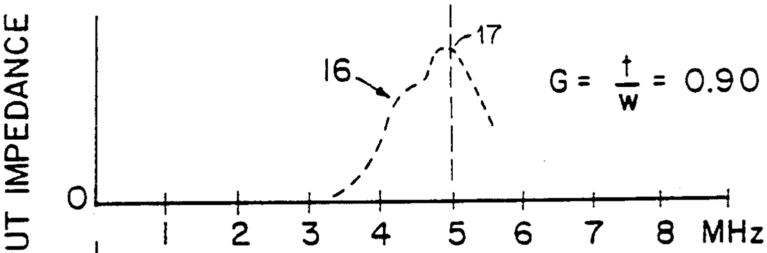
FIGS. 2 through 5 show how the electrical input impedance of a typical individual sensor element varies as a function of frequency.
Figure 3:
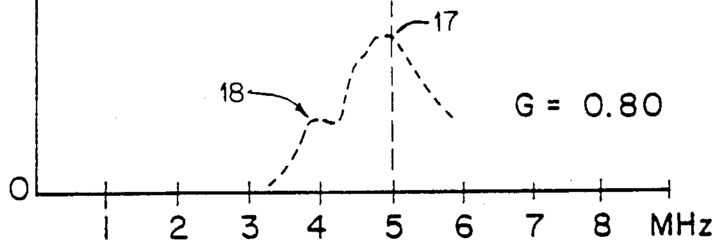

First of all, each element [10] is proportioned so that it will have a well defined resonance in the thickness dimension [12] and a well defined resonance in the width dimension [14], The resonance in the the thickness dimension [12] is the the desired frequency, and the resonance in the width dimension [14] is the dilatational frequency, $f_{dil}$. FIG. 2 indicates how the $f_{dil}$ [16] is close to the desired frequency [17] when the aspect ratio is 0.90, i.e. when the width is only slightly greater than the thickness. FIG. 3 indicates how, for an element having an aspect ratio of 0.80, the $f_{dil}$ [18] moves away from the desired frequency [17].

Figure 4:
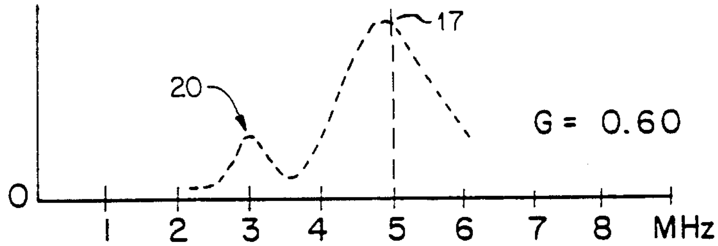
Figure 5:
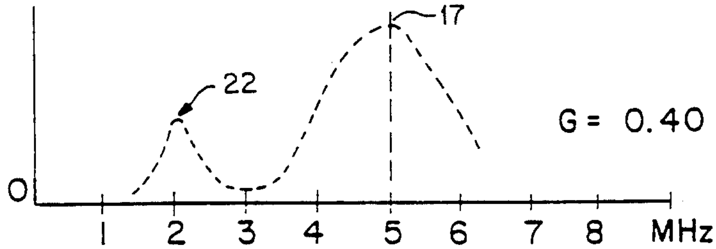

FIG. 4 indicates how the $f_{dil}$ [20] moves still further away from the desired frequency [17] as the aspect ratio decreases to 0.60. FIG. 5 shows how the $f_{dil}$ [22] moves even further from the desired frequency [17] for an aspect ratio of 0.40, i.e. when the width dimension [12] is 2.5 times the thickness dimension [12].

Figure 14:
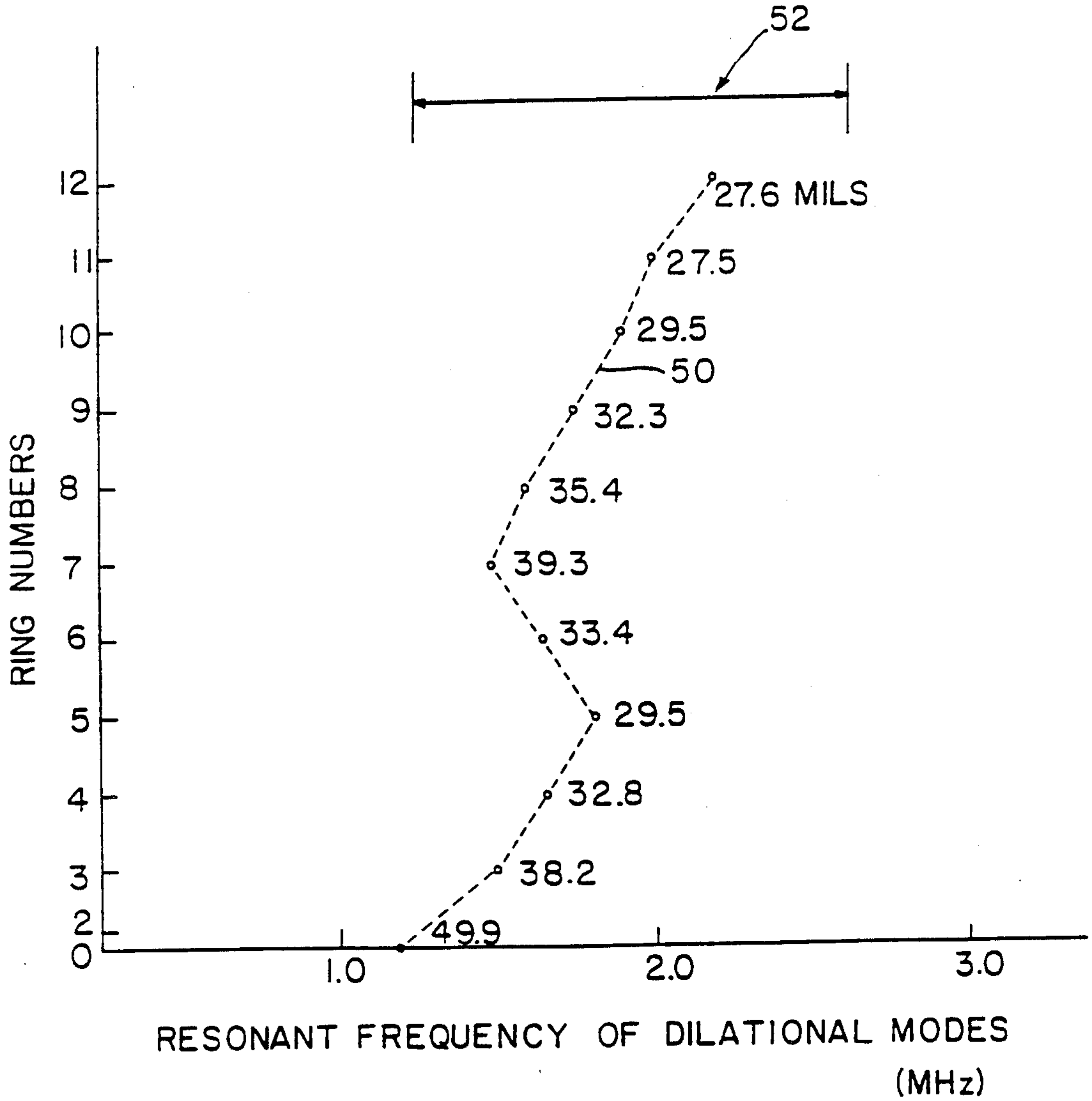
FIG. 14 shows the frequency of maximum dilatational response for each of the individual elements of an existing 12 element annular array in which no particular effort has been made to optimize the dilatational response frequencies. In this case, the resonant frequency of each element is somewhat different from that of each other element.

Secondly, each of the elements [10] is proportioned so that they all have essentially the same dilatational frequency $f_{dil}$. FIG. 14 indicates that, for an existing twelve element annular array, the dilatational frequencies [50] of each element [10] are only slightly different from each other, even though no attempt has been made to adjust the frequencies to be the same. In FIG. 14, it can be seen that the range [52] dilatational mode resonant frequencies $f_{dil}$ is from about 1.18 Mhz, at the center of the array [11] to about 2.18 Mhz at the outer edge of the annular array [11], with most of the element's $f_{dil}$ being clustered at about 1.6 Mhz.

It has been shown experimentally that the $f_{dil}$ of any element can be adjusted to fall at any desired frequency in this range by relatively small adjustments to its dimensions. For example, decreasing the width of a ring shaped element [10] having an $f_{dil}$ of 1.5 Mhz by 10 thousandths of an inch will increase its $f_{dil}$ to 1.9 Mhz.

Figure 15:
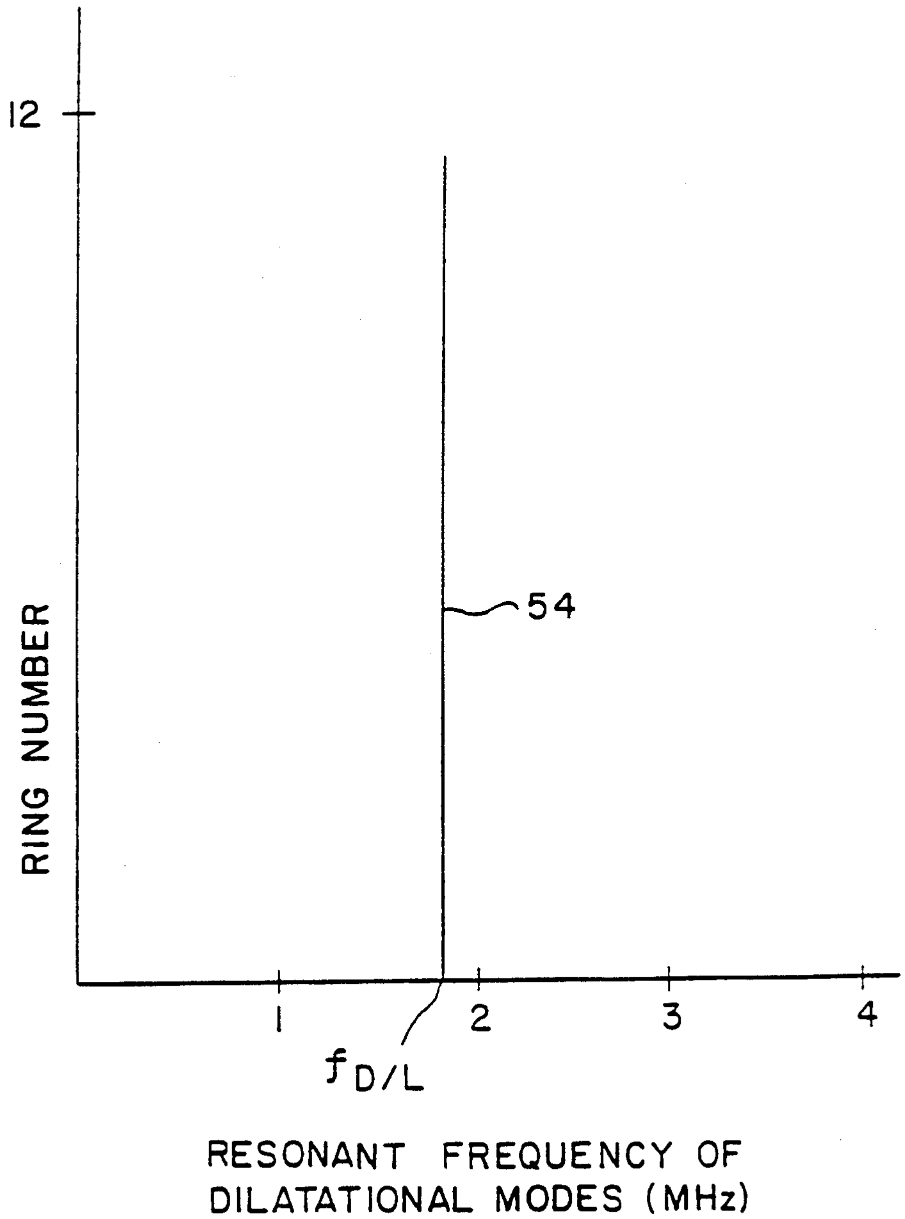
FIG. 15 shows how the frequency of dilatational response could be optimized, so that the frequency of maximum dilatational response would be essentially identical for each of the elements in the annular array. A similar optimization could be performed for the elements of a linear array.

FIG. 15 illustrates what would happen if each of the individual elements [10] were individually designed with a carefully adjusted aspect ratio. In this case, $f_{dil}$ [54] of each individual element [10] would be essentially the same.

Thirdly, the drive pulses are transmitted as well-defined pulse trains having a specific number of pulses. If necessary, the frequency of the drive pulses will be "fine tuned" to achieve the deepest possible null at the frequency of dilatational resonance.

Figure 6:
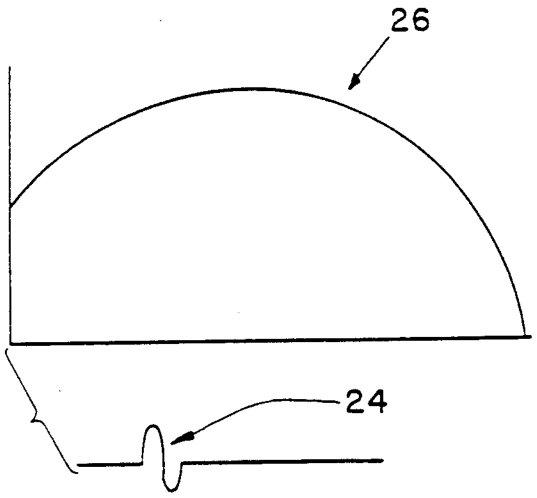
FIG. 6 shows the frequency content of a single-pulse train.
Figure 7:
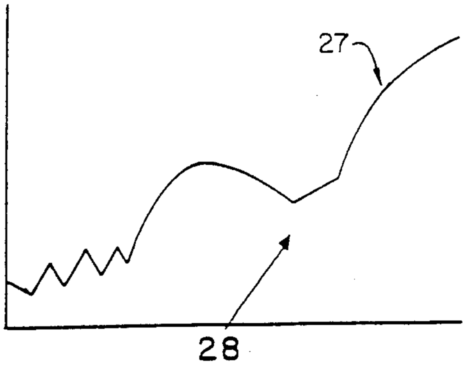
FIG. 7 shows the receiver response of an annular array sensor, when such a single pulse train is transmitted, and received from a target located in a water tank.
Figure 8:
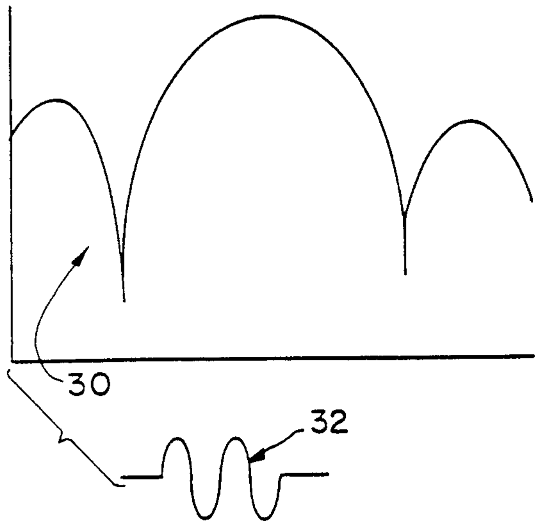
FIGS. 8 and 9 show the same information as FIGS. 6 and 7, respectively, for a two-pulse train. Similarly
Figure 9:
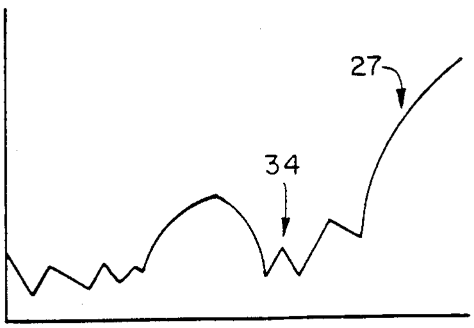

In what follows, pairs of Figures are shown, in which the first Figure illustrates the frequency spectrum of the transmitted pulse train, and the second Figure illustrates the frequency spectrum of the signal received back when that pulse train is transmitted into a standard ultrasonic target. FIG. 6 illustrates the transmitted frequency spectrum [26] of a single pulse wave train [24]. FIG. 7 shows the dilatational return in the received spectrum [27] below about 2.4 Mhz; the null [28] between the dilatational response and the desired response is not distinct. FIG. 8 illustrates the transmitted frequency spectrum [30] of a two pulse wave train [32]. FIG. 9 shows that the dilatational response is separated by a deeper null [34] in the received spectrum [27], so that the dilatational response is more distinct.

Figure 10:
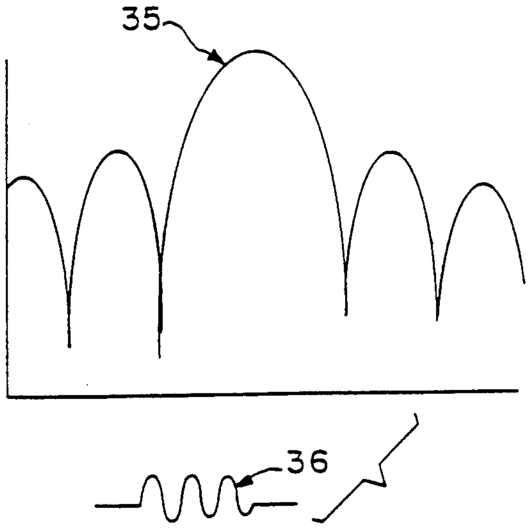
FIGS. 10 and 11 show this information for a three pulse train.
Figure 11:
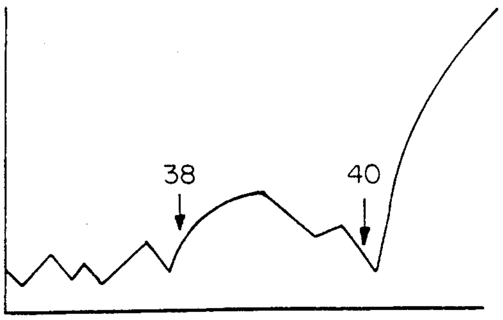

FIG. 10 illustrates the frequency spectrum [35] of a three pulse wave train [36]. FIG. 11 shows that there are two distinct dilatational responses separated by two nulls [38,40], so that the dilatational response is still further from, and more distinct from, the desired frequency response.

Figure 12:
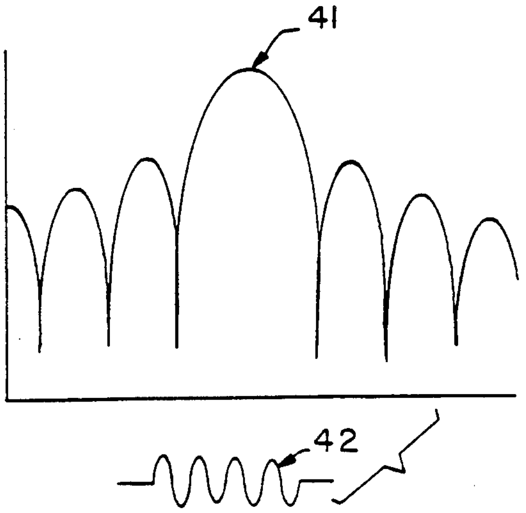
FIGS. 12 and 13 show the same information for a four-pulse train.
Figure 13:
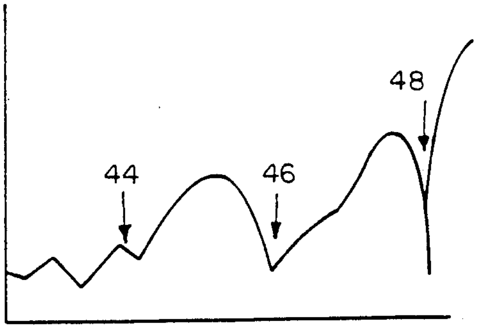

Finally, FIG. 12 shows the transmitted spectrum [41] of a four pulse wave train [42]. FIG. 13 indicates that there are 3 frequency regions in which the dilatational response is received, separated from the desired response by three nulls [44,46,48].

Figure 16:
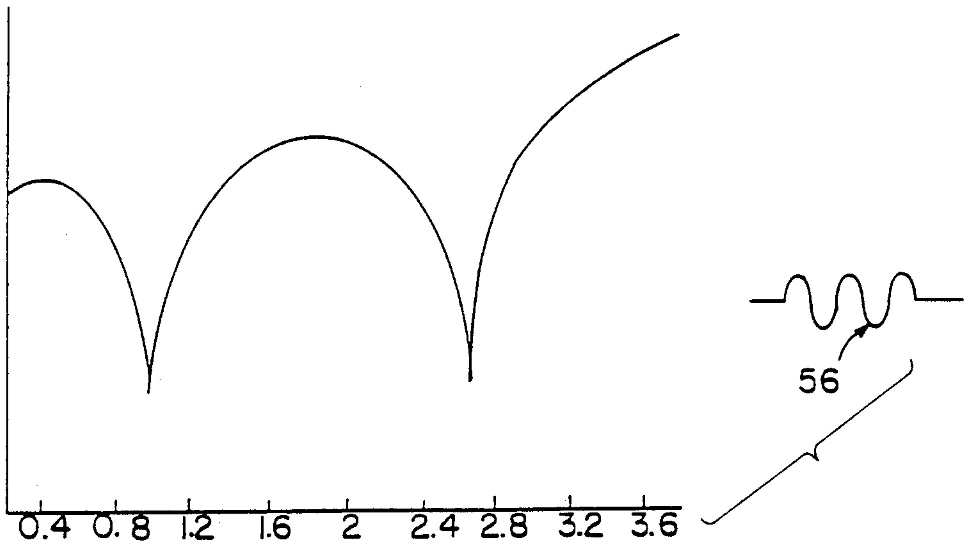
FIGS. 16 and 17 show the frequency content of pulse trains containing 2.5 and 3.5 pulses, respectively.
Figure 17:
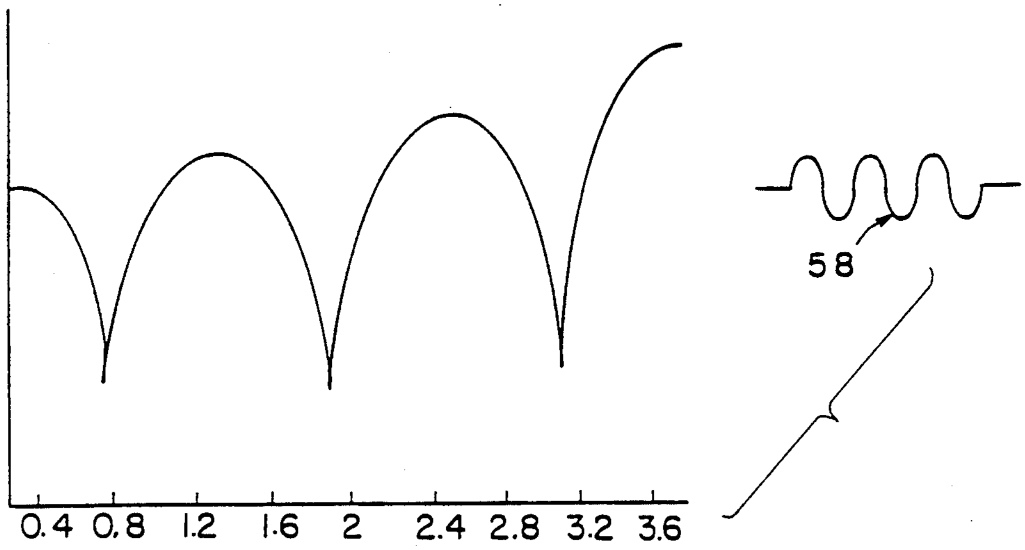

There may also be a fractional number of pulses, as shown in FIGS. 16 and 17, which show the frequency spectra corresponding to 2.5 [56] and 3.5 [58] pulses, respectively.

The whole or fractional number of transmitted pulses [24,32,36,42,56,58] is chosen so that the frequency spectrum of the pulse train has a null at the same frequency as the $f_{dil}$ of the sensor elements. Thus when the array is driven by a train of pulses having the correct number of pulses, essentially all the energy is transmitted at the primary, desired, resonance mode, and essentially no energy is transmitted at the dilatational modes of the sensor. The result is suppression of the undesired dilatational modes.

What is claimed is:

1. A method of reducing a dilatational response of an ultrasonic sensor (10) by:

a. fabricating at least one element (10) of said sensor (11) with a thickness dimension (12), and a width dimension (14);
   the ratio of said width dimension (14) to said thickness dimension (12) being such that a dilatational response of said thickness dimension (12) occurs at a specific frequency $f_{dil}$;
b. driving at least one element (10) of said ultrasonic sensor (11) with a train of drive pulses;

the number of pulses in said train being selected so that a frequency spectrum of said train has a null at said frequency $f_{dil}$.

2. A method of reducing a dilatational response of an ultrasonic sensor (11), as in claim 1, wherein said element (10) of said ultrasonic sensor (11) is an annular ring.

3. A method of reducing a dilatational response of an ultrasonic sensor (11), as in claim 2, wherein said ultrasonic sensor (11) is an annular array sensor.

4. A method of reducing a dilatational response of an ultrasonic sensor (11) as in claim 3, wherein each ring shaped element (10) of said sensor (11) is fabricated so that said dilatational frequency $f_{dil}$ of each element (10) is substantially identical.

5. A method of reducing a dilatational response of an ultrasonic sensor (11), as in claim 1, wherein said element (10) of said ultrasonic sensor (11) is a linear rectangular element.

6. A method of reducing a dilatational response of an ultrasonic sensor (11), as in claim 5, wherein said ultrasonic sensor (11) is a linear array sensor.

7. A method of reducing a dilatational response of an ultrasonic sensor (11), as in claim 6, wherein each ring shaped element (11) of said sensor (11) is fabricated so that said dilatational frequency $f_{dil}$ of each element (10) is substantially identical.

8. An ultrasonic sensor (11) in which dilatational modes are minimized,. comprising:

a. a means for producing a train of drive pulses having at least one selected variable null frequency (16); and b. at least one electroacoustic element (10); the element (10) being coupled to the drive means, wherein energy of the train of drive pulses is transferred from the drive means to the element (10); the element having width (14) and thickness (12) dimensions selected to fix a frequency of maximum dilatational response, $f_{dil}$; said null frequency (16) closely coinciding with $f_{dil}$.

9. An ultrasonic sensor (11) as in claim 8 in which said element (10) of said ultrasonic sensor (11) is a circular ring.

10. An ultrasonic sensor (11) as in claim 9 in which said ultrasonic sensor (11) is an annular array sensor.

11. An ultrasonic sensor (11) as in claim 10, in which said dilatational response $f_{dil}$ is substantially identical (54) for each of said elements (10).

12. An ultrasonic sensor (11) as in claim 8 in which said element (10) of said ultrasonic sensor (11) is a linear rectangular element.

13. An ultrasonic sensor (11) as in claim 12 in which said ultrasonic sensor (11) is a linear array sensor.

14. An ultrasonic sensor (11) as in claim 13, in which said dilatational response $f_{dil}$ is substantially identical (54) for each of said elements (10).

* * * * *